United States Patent [19]

Karasawa

[11] Patent Number: 4,649,917

[45] Date of Patent: Mar. 17, 1987

[54] RESECTOSCOPE WITH MATCHING MARKERS AND METHOD OF ASSEMBLY

[75] Inventor: Hitoshi Karasawa, Tokyo, Japan

[73] Assignee: Olympus Optical Co., Ltd., Tokyo, Japan

[21] Appl. No.: 679,468

[22] Filed: Dec. 7, 1984

[30] Foreign Application Priority Data

Dec. 26, 1983 [JP] Japan .............................. 58-203705

[51] Int. Cl.$^4$ ............................................ A61B 17/32
[52] U.S. Cl. ................................................ 128/303.14
[58] Field of Search .............. 128/674, 303.14, 303.17; 604/110

[56] References Cited

U.S. PATENT DOCUMENTS

| | | | |
|---|---|---|---|
| Re. 31,873 | 4/1985 | Howes .................................. | 128/674 |
| 1,971,024 | 8/1934 | Wappler .......................... | 128/303.17 |
| 4,150,673 | 4/1979 | Watt ..................................... | 604/110 |

OTHER PUBLICATIONS

ACMI Catheters and Accesories, pp. 32–35, American Cystoscope Makers, Inc., 1960.

Primary Examiner—William E. Kamm
Attorney, Agent, or Firm—Frishauf, Holtz, Goodman & Woodward

[57] ABSTRACT

A resectoscope comprises a plurality of sheaths having different inner diameters, a plurality of optical observation tubes having different view field directions and insertible into the corresponding sheaths, and a plurality of electrode rods which are provided with electrode sections bent at different angles for different view field directions and having different sizes and which are insertible into the corresponding sheath. A resectoscope is assembled from one selected sheath, one selected optical observation tube and one selected electrode rod. In order to facilitate the correct assembly of these various parts, the electrode rods have a first color mark capable of distinguishing the different angles of the electrode sections and a second color mark capable of distinguishing the different sizes of the electrode sections. The respective sheaths have a third color mark capable of distinguishing their different inner diameters. The optical observation tubes have a fourth color mark capable of distinguishing their different view field directions [and the]. The assembled electroscope combines an electrode rod, sheath and optical observation tube having suitably matching color marks.

9 Claims, 6 Drawing Figures

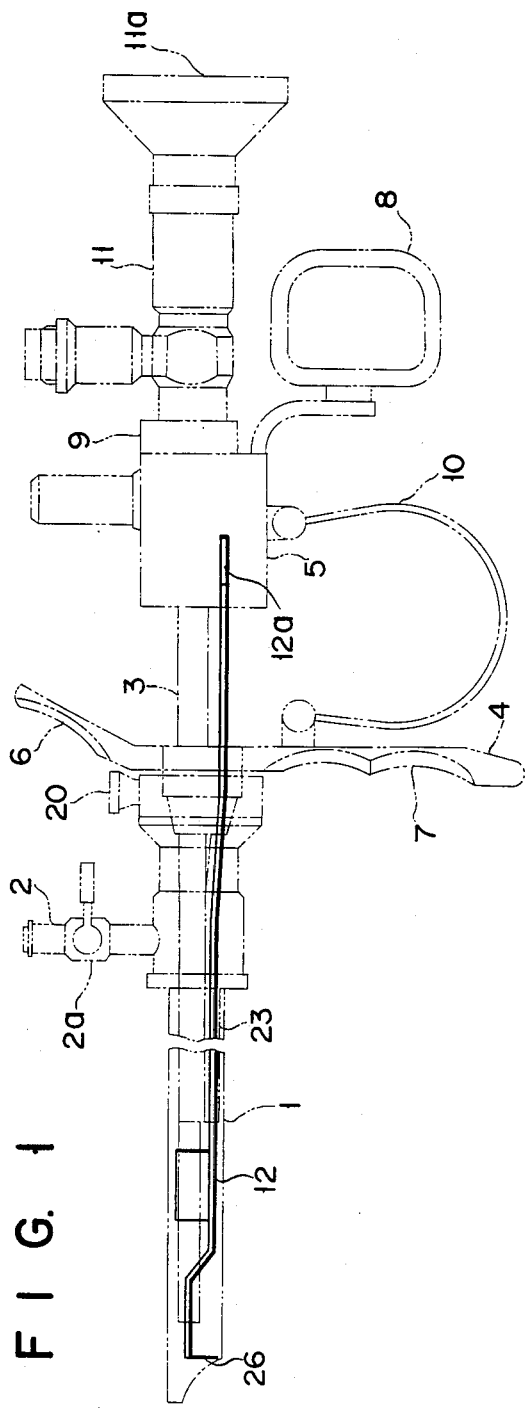
FIG. 1
FIG. 2A
FIG. 2B

RESECTOSCOPE WITH MATCHING MARKERS AND METHOD OF ASSEMBLY

BACKGROUND OF THE INVENTION

This invention relates to a resectoscope which cuts off the morbid portion of the prostate gland or bladder, while observing said morbid portion.

A resectoscope is known as a medical instrument for distingushing the morbid portion of the prostate gland or bladder by the eye and applying a medical treatment thereto.

This type of resectoscope is generally constructed by detachably inserting an electrode rod and optical observation tube into a sheath. The morbid portion of, for example, the prostate gland or bladder is burnt off by reciprocatively moving the electrode section formed at the distal end of the electrode rod through the distal end of the sheath. Concretely, the electrode section is made into a loop having substantially the same inner diameter as that of the sheath. Resection is carried out by clamping the morbid portion of the prostate gland or bladder between said looped electrode section and the distal end of the sheath.

The resectoscope is made to function with a thickness suitable for the examinee's body and a view field adapted to easily distinguish the position of the morbid portion of, for example, the prostate gland or bladder. Actually a plurality of optical observation tubes are provided for the respective intended view fields. Also, a plurality of sheaths having different thickness are provided. Further, a plurality of electrode rods are provided which are fitted with loops having different angles to match the intended view fields. Also, a plurality of electrode rods are provided which are fitted with loops having different diameters matching the inner diameters of sheaths to be applied, in order that the morbid portion of, for example, a prostate gland or bladder may be assuredly clamped between the distal end of the sheath and the loop of the electrode portion of the electrode rod. Selected from the above-mentioned various optical observation tubes, sheaths and electrode rods, are those types which match an examinee's body and the condition of said morbid portion of, for example, the prostate gland or bladder. Thus, it has been attempted to ensure the proper function of the resectoscope by assembling the electrode rod, optical observation tube and sheath so as to fit the condition of said morbid portion to be medically treated.

However, the above-mentioned assembly is accompanied with complexities, tending to give rise to errors, and consequently resulting in the drawback that a resectscope is applied which comprises wrongly assembled parts.

SUMMARY OF THE INVENTION

It is accordingly the object of this invention to provide a resectoscope which can avoid the erroneous assembly of the electrode rod, sheath and optical observation tube.

BRIEF DESCRIPTION OF THE DRAWINGS

FIG. 1 is a lateral view of a resectoscope embodying this invention;

FIG. 2A is a sectional view of an electrode rod;

FIG. 2B is a front view of an inserted electrode rod as taken from the front;

DETAILED DESCRIPTION OF THE PREFERRED EMBODIMENT

Figure 3:
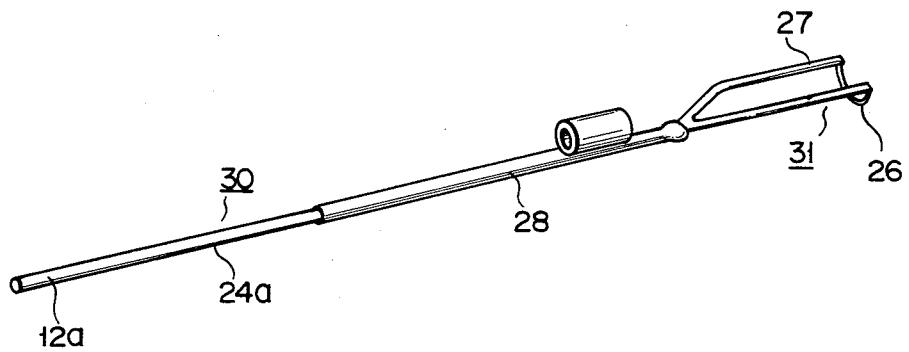
FIG. 3 is an oblique view of the electrode rod.

Description may now be made with reference to the accompanying drawings of a resectoscope embodying this invention.

FIG. 1 is a lateral view of said resectoscope. Reference numeral 1 denotes a sheath whose rear side is provided with an inlet port 2 allowing for the pouring of a liquid. Reference numeral 2a shows a valve fitted to said inlet port 2. Reference numeral 3 shows a guide tube. Fitted in parallel to said guide tube 3 is another tubular member 23 into which an electrode rod 12 is inserted. Provided on the rear side of the guide tube 3 is a slider 5 which reciprocates along the shaft of said guide tube 3. A scope 11 acting as an optical observation tube is detachably inserted into the guide tube 3 at its rear end. The electrode rod 12 is detachably inserted into the tubular member 23 at its front end. The electrode rod 12 is constructed by fitting an electrode 26 which is formed of a wire 25 made into a substantially U-shaped loop 25a to the distal end of a jig 24 covered with an insulation member 24a. Reference numeral 27 denotes an insulation member covering the wire 25. Reference numeral 28 represents a pipe covering the central portions of the insulation members 24a and 27. A conductor 12a provided at the rear end of the electrode rod 12 is connected to the inside of the slider 5, thereby enabling the whole electrode rod 12 to move back and forth with the reciprocation of the slider 5. An operation system is provided on the rear side of the guide tube 3 to assist the reciprocation of the slider 5. Said operation system comprises a forefinger-touched section 6 and a section 7 touched with the middle finger and ring finger, both sections 6, 7 being formed on both sides of the operation system. This operation system is further provided with a lever 4 fixed as the center to the rear portion of the guide tube 3, thumb-touched section 8 fitted to the slider 5 and a plate spring 10 stretched between the ring finger-touched section 7 and slider 5 in the U-form, thereby urging the slider 5 toward the rear side of the lever 4. The operation system is gripped by touching the finger section 6 with the forefinger, the finger section 7 with the middle finger and ring finger and the finger section 8 with the thumb. When the slider 5 is moved forward along the guide tube 3, the electrode rod 12 is pushed. The electrode rod 12 is retracted by the right movement of the plate spring 10. Reference numeral 9 represents a stopper fixed to the rear end of the guide tube 3 to prevent the slider 5 from moving backward.

The guide tube 3 containing the scope 11 and tubular member 23 are inserted into the sheath 1 at its rear end. Then the electrode rod 12 is inserted into said tubular member 23 at its front end and is fixed to the slider 5. As a result, the electrode section 12a formed at the distal end of the electrode rod 12 faces an opening formed at the distal end of the sheath 1. In this case, the sheath 1 constitutes the insertion section of the resectoscope.

Reference numeral 20 in FIG. 1 shows a coupler for effecting a detachable connection between the rear side of the sheath 1 and that portion of the guide tube 3 which lies immediately before the lever 4, thereby effecting the coupling of the sheath 1 with the guide tube 3 held therein.

With the above-mentioned resectoscope embodying this invention, sheaths 1 having different thicknesses, scopes 11 having different view field directions and electrode rods 12 having different diameters corresponding to the inner diameters of the respective sheaths 1 and whose distal end electrode sections are provided with loops bearing angles corresponding to the different view field directions of the scopes 11 can be all assembled in such a manner that said resectoscope carries out a function adapted for the elimination of the morbid portion of, for example, the prostate gland or bladder. For the manufacture of a resectoscope embodying this invention, there are provided a plurality of sheaths having different wall thicknesses, a plurality of scopes 11 having different view field directions, a plurality of electrode rods 12 whose distal end electrode portions are provided with loops 25a having diameters matching the inner diameters of the sheaths 1 and bearing such angles as shown by the one dot-dash lines given in FIG. 2. Selected from among the abovementioned various sheaths 1, scopes 11 and electrode rods 12 are the types which are adapted to cause the subject resectoscope to perform such a function as can effectively eliminate the morbid portion of, for example, the prostate gland or bladder.

Figure 4:
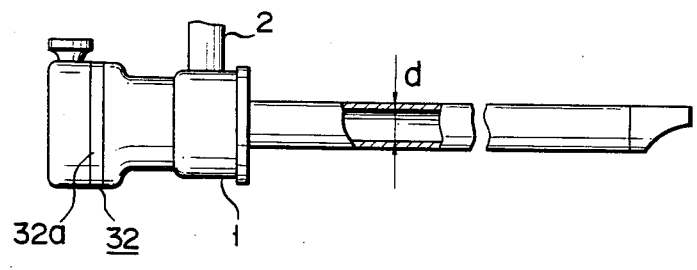
FIG. 4 is a lateral view of a sheath.
Figure 5:
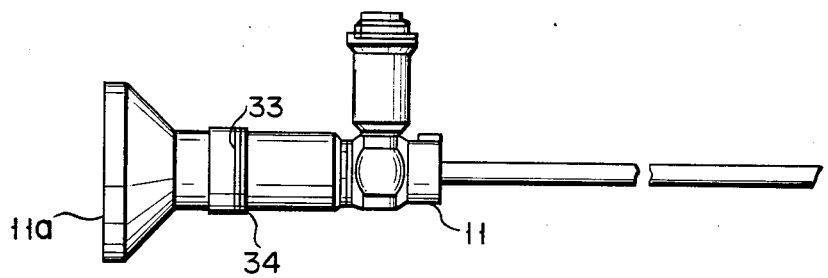
FIG. 5 is a lateral view of the resectoscope.

As seen from FIG. 3, the rear portion of the electrode rod 12 is provided with a first mark 30 which bears such a color as distinguished the rear insulation section 24a in accordance with the view field angle of the loop 25a of said electrode rod 12. The forward portion of the electrode rod 12 is provided with a second mark 31 which bears such a color as distinguishing the insulation member 27 covering the wire 25 in accordance with the diameter of the loop 25a of said electrode rod 12. As shown in FIG. 4, the rear shaft of the sheath 1 is provided with a sheath-distinguishing colored member 32a (a third mark 32) which bears such a color as representing the inner diameter d of the forward part of the sheath 1 acting as the insertion portion of the resectoscope. As indicated in FIG. 5, the shaft of the eyepiece 11a of scope 11 is provided with a colored scope-distinguishing member 33 (a fourth mark 34) which bears such a color as indicating a particular view field direction.

Selected from among the first mark 30 and second mark 31 of the electrode rod 12, the third mark 32 of the sheath 1 and the fourth mark 34 of the scope 11 are those types which ensure the proper assembly of the electrode rod 12 and sheath 1. Namely, a selection is made of that assembly from among the above-mentioned first, second, third and fourth marks 30, 31, 32, 34 which causes the diameter of the loop 25a and the inner diameter d of the sheath 1 to match each other. With respect to said selected assembly, the second mark 31 of the electrode rod 12 and the third mark 32 of the sheath 1, which have the same color are adopted. Further, a selection is made of that assembly from among said four marks 30, 31, 32, 34 which ensures the proper matching of the electrode rod 12 and scope 11. Namely, with respect to said selected assembly, which enables the angle of the loop 25a to properly match the view field direction of the scope 11, the first mark 30 of the electrode rod 12 and the fourth mark 34 of the scope 11 which have the same color are adopted. Thus, the proper assembly of the sheath 1, scope 11 and electrode rod 12 is determined by judging whether or not the group of the second mark 31 of the electrode rod 12 and the third mark 32 of the sheath have the same color, or the group of the first mark 30 of the electrode rod 12 and the fourth mark 34 of the scope 4 have the same color.

Now, the following assumption is made. Three scopes 11 are provided which indicate different view field directions represented by for example, 0°, 12° and 30°. The fourth mark 34 of the scope 11 indicating a view field direction of 0° bears a green color. The fourth mark 34 of the scope 11 indicating a view field direction of 12° bears a blue color. The fourth mark 34 of the scope 11 indicating a view field direction of 30° bears a red color. Three sheaths 1 are provided which have different thicknesses of, for example, 24Fr, 26Fr, and 28Fr. The third mark of the sheath 1 having the thickness of 24Fr bears a yellow color. The third mark of the sheath 1 having thickness of 26Fr bears a red color. The third mark of the sheath 1 having the thickness of 28Fr bears a black mark. Nine electrode rods 12 are provided to ensure matching with the three kinds of the scopes 11 and the three kinds of the sheaths 1. The first mark 30 of the electrode rod 12 selectively bears a green, blue or a red color to correspond to any of the above-mentioned three view field directions of the scope 11. The second mark 31 of the electrode rod 12 selectively bears a yellow, red or black color to correspond to any of the abovementioned three thicknesses of the sheath 1.

When it is attempted to let a resectscope perform a function adapted for the body of an examinee and the condition of the morbid portion of, for example, his prostate gland or bladder, the object is attained by selecting that type of the electrode rod 12 which matches the above-mentioned conditions, the scope 11 whose fourth mark 34 bears the same color as that of the first mark 30 of said electrode rod 12, and that type of sheath 1 whose third mark 32 bears the same color as that of the second mark 31 of the electrode rod 12 and assembling the selected electrode rod 12, scope 11 and sheath 1.

The assembly of the selected electrode 12 with the scope 11 differentiated according to the view field direction and the sheath 1 differentiated according to the thickness can be easily and reliably effected simply with reference to the selected colors of the first and second marks 30, 31 of the electrode rod 12 without any error.

With the foregoing embodiment, marks bearing different colors were used to effect the proper assembly of the electrode rod 12, scope 11 and sheath 1. However, this invention is not limited to this assembling process. But it is possible to apply marks represented by, for example, white and black patterns.

Further with the above-mentioned embodiment, the first mark was provided at the rear side of the electrode rod 12 and the second mark was formed at the distal side of said electrode rod 12. The assembly of the electrode rod 12 with the sheath 1 was effected with reference to the second mark of said electrode rod 12, and the assembly of the electrode rod 12 with the scope 11 was carried out with reference to the first mark of said electrode rod 12. However, it is possible to effect the assembly of the electrode rod 12 with the scope 11 conversely with reference to the second mark of said electrode rod 12 and perform the assembly of the electrode rod 12 with the sheath 1 with reference to the first mark of the electrode rod 12.

As described above, this invention enables the sheath and scope to be distinctly assembled with the electrode rod without any error, thereby preventing a resectoscope from being applied with the erroneous assembly of said three components.

What is claimed is:

1. A method for assembling a resectoscope from a supply of parts including a plurality of sheaths having different respective inner diameters, a plurality of optical observation tubes having different respective view field directions and which are insertible into a corresponding sheath, and a plurality of electrode rods respectively having different sizes and different view field directions and which are insertible into a corresponding sheath, said method comprising the steps of:

providing each electrode rod with a first mark indicative of its angle for the view field direction;
providing each electrode rod with a second mark indicative of its size;
providing each sheath with a third mark indicative of its inner diameter;
providing each optical observation tube with a fourth mark indicative of its view field direction; and
selecting an electrode rod, a sheath, and an optical observation tube such that the first mark matches the fourth mark and the second mark matches the third mark.

2. The method of claim 1, wherein the first mark and fourth mark are the same, and wherein the second mark and third mark are the same.

3. The method of claim 1, wherein the second mark and third mark are the same.

4. The method of claim 1, wherein the first mark and the fourth mark are the same.

5. In a resectoscope apparatus including a sheath, an electrode rod inserted in said sheath, and an optical observation tube coupled to one end of said sheath, said sheath being selected from a number of sheaths having different respective inner diameters, said optical observation tube being selected from a number of optical observation tubes having different respective new field directions, said electrode rod being selected from a number of electrode rods provided, respectively, with electrode sections bent at different angles for different view field directions and having different respective sizes, the improvement comprising:

first marking means on the electrode rod for distinguishing the angle of its electrode section from the angles of the electrode sections of other electrode rods;
second marking means on the electrode rod for distinguishing the size of its electrode section from the size of the electrode section of other electrode rods;
third marking means on the sheath for distinguishing its inner diameter from the inner diameter of other sheaths; and
fourth marking means on the optical observation tube for distinguishing its view field direction from the view field direction of other optical observation tubes;
said first marking means matching said fourth marking means, and said second marking means matching said third marking means.

6. The resectoscope apparatus of claim 5, wherein said first marking means includes at least one color to distinguish its angle of the electrode section, and the fourth marking means includes at least one color to distinguish its view field direction, said one color of the fourth marking means being the same as the said one color of said first marking means.

7. The resectoscope apparatus according to claim 6, wherein said electrode rod comprises a rear portion having the first marking means therein and a distal portion having the second marking means therein.

8. The resectoscope apparatus of claim 7, wherein said second marking means includes at least one color to distinguish its size, and the third marking means includes at least one color to distinguish its inner diameter, said one color of the second marking means being the same as said one color of the third marking means.

9. The resectoscope apparatus of claim 6, wherein said second marking means includes at least one color to distinguish its size, and the third marking means includes at least one color to distinguish its inner diameter, said one color of the second marking means being the same as said one color of the third marking means.

* * * * *